(12) United States Patent
López-Cabrera et al.

(10) Patent No.: US 6,780,436 B1
(45) Date of Patent: Aug. 24, 2004

(54) SOLID ORAL PHARMACEUTICAL FORMULATION OF MODIFIED RELEASE THAT CONTAINS AN ACID LABILE BENZIMIDAZOLE COMPOUND

(75) Inventors: Antonio López-Cabrera, Barcelona (ES); Pedro Juan Solanas-Ibarra, Barcelona (ES); Vincent Mancinelli, Morgantown, WV (US)

(73) Assignee: Laboratorios Del Dr. Esteve, SA, Barcelona (ES)

(*) Notice: Subject to any disclaimer, the term of this patent is extended or adjusted under 35 U.S.C. 154(b) by 0 days.

(21) Appl. No.: 09/660,022

(22) Filed: Sep. 12, 2000

(30) Foreign Application Priority Data

Sep. 13, 1999 (ES) ................................................ 9902027

(51) Int. Cl.$^7$ .......................... A61K 9/14; A61K 9/16; A61K 9/20; A61K 9/50; A61K 9/52
(52) U.S. Cl. .................... 424/490; 424/457; 424/458; 424/459; 424/461; 424/462; 424/472; 424/480; 424/482; 424/489; 424/490; 424/493; 424/494; 424/495
(58) Field of Search ................................. 424/457, 458, 424/459, 461, 462, 464, 472, 480, 482, 489, 490, 493, 494, 495, 451

(56) References Cited

U.S. PATENT DOCUMENTS

| | | | |
|---|---|---|---|
| 4,150,111 A | 4/1979 | Warren et al. | 424/35 |
| 4,287,221 A | 9/1981 | Tonedachi et al. | 427/3 |
| 4,335,099 A | 6/1982 | Funakoshi et al. | 424/32 |
| 4,377,568 A | 3/1983 | Chopra | 424/31 |
| 4,470,980 A | 9/1984 | Higuchi et al. | 424/232 |
| 4,786,505 A | 11/1988 | Lovgren et al. | 424/468 |
| 5,232,706 A | 8/1993 | Palomo Coll | 424/475 |
| 5,395,611 A | 3/1995 | Jimbow | 424/62 |
| 5,445,829 A * | 8/1995 | Paradissis et al. | 424/480 |
| 5,626,875 A | 5/1997 | Ballester Rodes et al. | 424/464 |
| 5,817,338 A | 10/1998 | Bergstrand et al. | 424/468 |
| 5,945,124 A * | 8/1999 | Sachs et al. | 424/472 |
| 6,068,856 A * | 5/2000 | Sachs et al. | 424/474 |
| 6,077,541 A | 6/2000 | Chen et al. | 424/480 |

FOREIGN PATENT DOCUMENTS

| | | |
|---|---|---|
| EP | 0122815 | 10/1984 |
| EP | 0244380 | 11/1987 |
| EP | 0277741 | 8/1988 |
| EP | 0519144 | 12/1992 |
| EP | 0 773 025 A1 * | 5/1997 |
| EP | 0960620 | 12/1999 |
| GB | 829055 | 2/1960 |
| JP | 57208155 | 12/1982 |
| WO | 9222284 | 12/1992 |
| WO | 9601623 | 1/1996 |
| WO | 9601624 | 1/1996 |
| WO | 9852547 | 11/1998 |
| WO | 9852564 | 11/1998 |
| WO | 9853803 | 12/1998 |
| WO | 9948498 | 9/1999 |
| WO | 0009497 | 2/2000 |
| WO | 0012064 | 3/2000 |
| WO | 0027366 | 5/2000 |

OTHER PUBLICATIONS

Coating of Drugs, Up–to–Date Pharmaceutical Technology Series "No. 1", (1996) pp 1–2, Jiji Printing Co.
Hagars Handbuch Der Pharmazeutischen Praxis, (1971) pp. 760.
The United States Pharmacopeia, The National Formulary, (1994) pp. 2313.

* cited by examiner

*Primary Examiner*—Susan T. Tran
(74) *Attorney, Agent, or Firm*—Ladas & Parry

(57) ABSTRACT

The pharmaceutical formulation consists of a number of pellets that comprise an inert nucleus, a layer with the active ingredient, one or more intermediate layers that comprise at least a system of modified release, and an external layer of enteric coating. These pellets can be obtained applying the different layers by means of fluid bed coating techniques using aqueous solutions or suspensions of the components of such layers. The pharmaceutical formulations can be hard gelatin capsules or tablets and are suitable for use in the prevention and treatment of disorders related to abnormal gastric acid secretion.

24 Claims, No Drawings

SOLID ORAL PHARMACEUTICAL FORMULATION OF MODIFIED RELEASE THAT CONTAINS AN ACID LABILE BENZIMIDAZOLE COMPOUND

FIELD OF THE INVENTION

The invention relates to new pharmaceutical formulations that contain an acid labile benzimidazole compound, suitable for oral administration, constituted of a number of pellets that comprise the active ingredient, one or more intermediate layers that comprise, at least, a system of modified release, and an external enteric coating. The invention also refers to the procedure for the production of said pellets and pharmaceutical formulations and to the use thereof in Medicine.

BACKGROUND OF THE INVENTION

The compound, 5-methoxy-2[[(4-methoxy-3,5-dimethyl-2-pyridinyl)methyl]sulphinyl]-1H-benzimidazole, is a benzimidazole compound suitable for inhibiting the gastric secretion in mammals. In particular, it is suitable for the prevention and treatment of disorders related with the secretion of gastric acid, for example, gastric ulcer, duodenal ulcer, reflux esophagitis, Zollinger-Ellison syndrome, etc. Other benzimidazole compounds with anti-ulcer activity are pantoprazole, lansoprazole and rabeprazole.

Omeprazole, just as is the case with other benzimidazole compounds that have therapeutic interest, is an acid labile compound. This causes numerous problems when it comes to developing a pharmaceutical formulation for oral administration due to the fact that when said compound comes into contact with the stomach content, which is a strongly acidic environment, degradation occurs. This lability may be responsible for the variability of the intra- and inter-individual therapeutic response of omeprazole.

To avoid contact between acid labile compounds and gastric juice after oral administration of said compounds, solid pharmaceutical formulations have been developed that comprise a nucleus that contains the acid labile compound and an external layer that constitutes a gastro-resistant coating that may be separated by one or more intermediate layers. In some cases, conventional enteric coatings of acidic nature cannot be used because the active compound would decompose on contact, either direct or indirect, with this coating. This would be evidenced by a colour change and by a reduction in the amount of active compound after a time.

There are several ways of solving the problem related to the stability of the active compound. One of these consists of creating an alkaline environment around the acid labile benzimidazole compound, which is achieved using alkaline salts of the benzimidazole compound and/or incorporating a compound of alkaline reaction in the pharmaceutical gastro-resistant preparation [see, for example, European patent application EP 0 244 380 and the U.S. Pat. No. 4,786,505]. Another way of solving the problem of stability of the active compound is based on the creation of a physical barrier that manages a complete separation between the active compound and the enteric layer, thus avoiding any degradation of the active compound, and comprises the use of acceptable pharmaceutical excipients except those that give an alkaline reaction [see, for example, European patent EP 0 773 025].

The European patent application EP 0 244 380 describes pharmaceutical formulations suitable for oral administration of acid labile substances that comprise (a) a nucleus that contains the active substance along with a compound of alkaline reaction, (b) one or several inert intermediate layers that contain the excipients for the tablets that are soluble in water and which disintegrate quickly in water, a polymer forming a film soluble in water optionally along with compounds of alkaline reaction that act as regulators of pH between the nucleus and the external layer, and (c) an external layer consisting of an enteric coating.

The U.S. Pat. No. 4,786,505 describes pharmaceutical formulations suitable for oral administration of omeprazole that comprise (a) a nucleus that comprises omeprazole and a compound of alkaline reaction, an alkaline salt of omeprazole and a compound of alkaline reaction, or only an alkaline salt of omeprazole, (b) one or several inert intermediate layers soluble in water or that disintegrate quickly in water, and (c) an external layer consisting of an enteric coating.

The U.S. Pat. No. 5,626,875 describes pharmaceutical formulations suitable for the oral administration of acid labile benzimidazole compounds that comprise (a) a nucleus formed of inert granules, the active compound, an inert polymer soluble in water and excipients that do not exhibit alkaline reactions, (b) an inert layer coating the aforementioned nucleus, formed from a polymer soluble in water and non-alkaline excipients, and (c) an external layer consisting of an enteric coating.

Other pharmaceutical formulations of benzimidazole compounds are described in the PCT patent applications: WO 96/01623, which describes a form of dosing comprised of multiple units that contain omeprazole or an alkaline salt thereof, and that is composed of units deployed in the form of layers, individually covered with an enteric coating, that contain the active compound. These units deployed in the form of enterically covered layers are mixed with excipients for tablets that are then compressed together; and WO 96/01624, that describes a form dosing comprised of multiple units similar to that described in the application PCT WO 96/01623 that contains, by way of the active ingredient, an inhibitor of $H^+K^+$-ATPase [proton pump], labile in acid medium, for example, omeprazole, lansoprazole or pantoprazole.

One problem associated with some pharmaceutical formulations for oral administration of acid labile benzimidazole compounds is related to the plasma half life of the active ingredient. In general, the plasma concentration of omeprazole, administered by means of hard gelatin capsules that contain omeprazole pellets with enteric coating, is at peak 2 hours after administration, with a gradual tailing off at later times. This leads to large fluctuations in the concentration of the active ingredient in blood and tissues that in turn leads to the need to carry out frequent administrations of the medicament to maintain a suitable therapeutically effective concentration.

As is known, in order that a certain active ingredient can act in a therapeutically effective manner it is necessary to reach a concentration in blood lying within the range known as the "effective concentration". The concentration in blood of the active ingredient at levels greater than the effective concentration tends to increase the incidence of secondary effects, while concentrations below the effective concentration level would result in a weak or null pharmacological response. With a target to obtain an active ingredient blood concentration level lying within the effective concentration range, different solid pharmaceutical formulations have been developed with modified release that allow the release and absorption of the active ingredient to be adjusted with respect to biotransformation thereof and elimination thereof from the organism, thus allowing the secondary effects to be reduced and prolonging the action of the active ingredient. Despite the numerous advantages that solid pharmaceutical formulations of modified release enjoy not many such pharmaceutical formulations have been described for the administration of omeprazole or other acid labile benzimidazole compounds.

The patent application PCT WO 98/52547 describes a pharmaceutical formulation of an active ingredient, for example, an inhibitor of the proton pump such as omeprazole, suitable for oral administration thereof, that comprises a composition for the controlled release of an active ingredient in the gastric environment during a prolonged period of time consisting of microspheres that comprise an active ingredient in the interior nucleus of the microsphere, a layer controlling the rate of release of the active ingredient consisting of a polymer insoluble in water, and an external layer of a bioadhesive agent in the form of a cationic polymer. In general, these formulations act by releasing the active ingredient in the gastric environment during a prolonged period of time and adhesion thereof to the mucus membranes is achieved It would therefore be worthwhile to develop new solid oral pharmaceutical formulations of modified release that increase the arsenal of media that allow effective administration of acid labile benzimidazole compounds. However, due to the characteristics of this type of active ingredient, compounds of an acid nature cannot be used as they might lead to the decomposition of the active ingredient.

DETAILED DESCRIPTION OF THE INVENTION

The invention provides a solid pharmaceutical formulation of modified release that contains an acid labile benzimidazole compound as an active ingredient, suitable for oral administration, hereinafter the pharmaceutical formulation of the invention, that comprises a number of pellets that contain the active ingredient, one or more intermediate layers that comprise, at least, a system of sustained release, and an external enteric coating.

In the sense used in this description, the term "acid labile benzimidazole compound" includes the benzimidazole compounds of therapeutic interest whose half life (i) is less than 10 minutes in an aqueous solution that has a pH less than 4, and/or (ii) lies between 10 minutes and 65 hours in an aqueous solution that has a pH of 7, for example, omeprazole, lansoprazole, pantoprazole, rabeprazole, as well as the compounds to which reference was made in the patent application PCT WO 97/12581.

In a particular embodiment, said acid labile benzimidazole compound is a 2[(2-pyridinyl)methylsulphinyl]benzimidazole compound of formula (I)

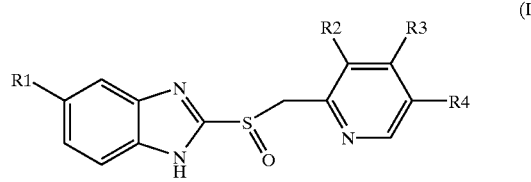

(I)

where
$R^1$ is hydrogen, methoxy or difluoromethoxy,
$R^2$ is methyl or methoxy,
$R^3$ is methoxy, 2,2,2-trifluoroethoxy or 3-methoxypropoxy, and
$R^4$ is hydrogen or methyl.

The active pellets, of modified release and gastro-resistant, that contain an acid labile benzimidazole compound as active ingredient, provided by this invention, hereinafter the pellets of the invention, comprise:

an inert nucleus;

an active layer, deposited over said inert nucleus (a), formed by an acid labile benzimidazole compound, an inert polymer, non-alkaline, soluble in water, and one or more pharmaceutically acceptable inert excipients;

one or more intermediate layers that comprise a non-alkaline inert coating, formed of an inert polymer, non-alkaline, soluble in water and one or more pharmaceutically inert excipients; and a system of modified release that comprises an inert polymer, non-alkaline, soluble in water and an inert polymer, non-alkaline, insoluble in water; said intermediate layer or layers being deployed over said active layer (b) that covers the inert nucleus; and an external layer deployed over said intermediate layer or layers (c) that consists of an enteric coating.

In a particular embodiment, the intermediate layer or layers (c) of the pellets of the invention, contain, separately:

one or more layers that constitute said non-alkaline inert coating; and one or more layers that contain said system of modified release.

In this particular embodiment said inert coating layers and modified release layers are separated from each other and constitute independent layers. Similarly, the number of layers of inert coating and the number of layers of modified release is variable, as is the order in which these layers appear. They may appear in alternating fashion. In a simple realization, the pellets of the invention included within this particular embodiment comprise a single inert coating layer and a single layer of modified release. A representative example of this particular embodiment of the invention is constituted of some gastro-resistant pellets of modified release, that contain an acid labile benzimidazole compound as active compound, that comprises:

an inert nucleus an active layer, deposited over said inert nucleus (a), formed by an acid labile benzimidazole compound, an inert polymer, non-alkaline, soluble in water, and one or more pharmaceutically acceptable inert excipients.

(c1) an intermediate layer that constitutes a non-alkaline inert coating deployed over said active layer (b) that covers the inert nucleus, formed from an inert polymer, non-alkaline, soluble in water and one or more pharmaceutically acceptable inert excipients;

(c2) an intermediate layer of modified release, deposited over said inert intermediate layer (c1) that comprises an inert polymer, non-alkaline, soluble in water and an inert polymer, non-alkaline, insoluble in water; and (d) an external layer deployed over said intermediate layer of modified release (c2) that consists of an enteric coating.

In another particular embodiment, the intermediate layer or layers (c) of the pellets of the invention, contain, mixed among themselves:

said non-alkaline inert coating; and said system of modified release.

In this particular embodiment said layers of inert coating and modified release are mixed among themselves and constitute a single layer of variable thickness. A representative example of this particular embodiment of the invention is constituted of some gastro-resistant pellets of modified release, that contain an acid labile benzimidazole compound as active compound, that comprises:

an inert nucleus;

an active layer, deposited over said inert nucleus (a), formed by an acid labile benzimidazole compound, an inert polymer, non-alkaline, soluble in water, and one or more pharmaceutically acceptable inert excipients.

An intermediate layer that comprises (i) an inert non-alkaline coating, soluble in water and one or more inert pharmaceutically acceptable excipients, and (ii) a system of modified release that comprises an inert non-alkaline polymer, soluble in water and an inert non-alkaline polymer, insoluble in water, this intermediate layer being deployed over said active layer (b) that covers the inert nucleus; and an external layer deployed over said intermediate layer (c) that consists of an enteric coating.

Another particular embodiment contemplated within the scope of the present invention comprises a "mixed" pellet, that is to say, a pellet of the invention in which said intermediate layer or layers (c) comprise a mixture formed by (1) one or more layers of inert coating and one or more layers of modified release, and (2) a mixture consisting of said inert coating and said system of modified release.

The inert nucleus (a) is a pharmaceutically inert substance in relation to the active ingredient, that is to say, it does not react with the active ingredient in the conditions used in such a way that there is decomposition thereof, and it may be composed of a sugar, for example, saccharose, starch and mixtures thereof. In a particular embodiment, said inert nuclei are composed of a mixture of saccharose and corn starch, have an average size lying between 0.3 and 1.4 mm and comply with the requirements of the USP (United States Pharmacopeia) [Monograph of Sugar Spheres, USP NF 18]. In a particular embodiment, the inert nuclei (a) are present in the pellet of the invention in an amount lying between 20% and 70% by weight with respect to the total pellet weight The active layer (b) comprises (i) an acid labile benzimidazole compound, preferably a compound of formula (I), more preferably omeprazole, (ii) an inert polymer, soluble in water and non-alkaline, such as hydroxypropylmethylcellulose (HPMC) or hydroxypropylcellulose (HPC) and (iii) one or more pharmaceutically acceptable excipients, such as an anti-tack or diluent, for example, talc. In the sense used in this specification the term "inert", applied to a polymer or an excipient, refers to the fact that said compounds do not react in the conditions used. In a particular embodiment, the active layer (b) is present in the pellet of the invention in an amount lying between 10% and 50% by weight with respect to the total pellet weight.

As has been mentioned earlier, the intermediate layer or layers (c) comprise one or more layers of inert coating and one or more layers of modified release (that is to say, those that contain the modified system of liberation), separated from each other forming one or more intermediate layers or else mixed among themselves forming a single intermediate layer or else a mixed system combining both realizations. In a particular embodiment, the intermediate layer or layers (c) is/are present in an amount lying between 5% and 30% by weight with respect to the total pellet weight.

The layer or layers of inert coating comprise (i) an inert polymer, non-alkaline, soluble in water, such as HPMC or HPC and (ii) one or more inert pharmaceutically acceptable excipients, such as an anti-tack or diluent, for example, talc, and a pigment or opacifier, for example, titanium dioxide.

The layer or layers of modified release comprise(s) a system of modified release that comprises an inert polymer, non-alkaline, insoluble in water, for example ethyl-cellulose (EC) or a copolymer of ammonium methacrylate [Eudragit® RS and RL30D] or any other excipient suitable to modify active ingredient release, along with an inert polymer, non-alkaline, soluble in water such as HPMC, and a plasticizer, for example dibutyl sebacate or similar plasticizers, and an anti-tack agent such as fumed silica or talc. This/these layer(s) provide the retarding character and the modified release of the active compound. The ratio of insoluble polymer:soluble polymer present in this/these layer(s) can vary between very wide limits. Varying the amount of insoluble polymer with respect to the soluble polymer gives a greater or lesser retarding effect [in general, increasing the amount of insoluble polymer with respect to the amount of soluble polymer leads to a slower release of the active ingredient]. In a particular embodiment, the system of modified release is present in the pellet of the invention, typically, in an amount between 5% and 15% with respect to the weight of the pellet.

The external layer (d) deployed over said intermediate layer or layers (c) constitutes the enteric coating and is composed of (i) a gastro-resistant polymer, such as a methacrylate copolymer, for example a copolymer formed by methacrylic acid and esters of methacrylic acid, (ii) a plasticizer, for example, triethyl citrate or similar plasticizers, and (iii) one or more pharmaceutically acceptable inert excipients, for example, talc. In a particular embodiment, the external layer (d) that constitutes the enteric coating is present in the pellet of the invention in an amount lying between 10% and 15% by weight with respect to the total pellet weight The pellets of the invention can be obtained by conventional techniques. A review of the different methods for obtaining pellets for pharmaceutical purposes can be found in the book *Pharmaceutical Pelletization Technology*, edited by Isaac Ghebre-Sellassie, Marcel Dekker, Inc., 1989. In a particular embodiment, the pellets of the invention are obtained applying the different layers by means of conventional fluid bed coating techniques using aqueous solutions or suspensions of the components of such layers. Briefly, in a fluid bed apparatus the inert nuclei are covered with first a layer that contains the acid labile benzimidazole compound, an inert polymer, non-alkaline, soluble in water, such as HPMC or HPC, and one or more inert pharmaceutically acceptable excipients, for example, talc. Then, said active layer is covered with one or more intermediate layers that contain (i) an inert non-alkaline coating, formed by an inert non-alkaline polymer, soluble in water, such as HPMC or HPC, and one or more pharmaceutically acceptable excipients, for example, talc and a pigment or opacifier, such as titanium dioxide; and (ii) a system of modified release that comprises an inert, non-alkaline polymer, soluble in water, such as HPMC, and an inert, non-alkaline polymer, insoluble in water, for example, EC or a copolymer of ammonium methacrylate or any other excipient suitable to modify active ingredient release. This intermediate layer can be formed of a variable number of layers of inert coating and of a variable number of layers of modified release separated, or else it can be formed by a single layer consisting of a mixture of the layers of inert coating and of modified release, or else by a mixture of both types. Finally, the layer of enteric coating is applied which consists of a polymer or copolymer resistant to gastric juice, such as that constituted by methacrylic acid and esters of methacrylic acid, a plasticizer, for example, triethyl citrate, and one or more inert pharmaceutically acceptable excipients, for example, talc.

The pellets of the invention can be administered in an appropriate pharmaceutical formulation, such as a solid pharmaceutical formulation, suitable for oral administration, for example, in the form of hard gelatin capsules or they may be formulated as tablets. The pharmaceutical formulation may contain pellets with different profiles of modified release, that is to say, with systems of modified release that have a differently weighted ratio (insoluble polymer:soluble polymer), for example, they may contain a mixture of (i) pellets with a fast release profile and (ii) pellets with a slow release profile, in a ratio (i):(ii), by weight, lying between 5:95 and 95:5, preferably 10:90 and 90:10. The pellets with a slow release profile comprise a ratio of insoluble polymer:soluble polymer in the system of modified release greater than in the case for pellets with a fast release profile. In the sense used in this description, the term "pellets with a slow release profile" refers to pellets that release in aqueous medium, pH 6.8, after 30 minutes [that is to say, 150 minutes if the 2 hours in acid medium (HCl) are counted according to Monograph 724 of the USP for "Drug Release", in particular, for Delayed-Release (Enteric coated Articles)] a maximum of 50% of the active ingredient. If the amount of active ingredient release in such conditions is greater than 50% then said pellets are considered, for the purposes of this specification, as "pellets with a fast release profile". Example 8 shows some illustrative data of pellets with slow release profiles and fast release profiles according to the present invention.

Therefore, the invention provides a solid pharmaceutical formulation of modified release that contains an acid labile benzimidazole compound as active ingredient, suitable for oral administration, that comprises a number of the pellets of the invention, with the same or different release profiles, in a therapeutically effective amount. The pharmaceutical formulation of the invention can be obtained by conventional methods depending on the exact administration form. A review of the different methods for obtaining pharmaceutical formulations is mentioned in the *Tratado de Farmacia Galénica* (Treatise on Pharmaceutical Formulation), C. Fauli i Trillo, Luzán S, S. A. de Ediciones (1993).

The active ingredients can be administered in the same dose and according to the same protocols as those employed for the existing commercial pharmaceutical formulations. In general, the dose of said active ingredient lies between approximately 1 mg/kg/day and 100 mg/kg/day, adjusted to the individual needs of the patients and according to the criterion of the specialist.

The pharmaceutical formulation of the invention is resistant to being dissolved in acid medium, is stable when passing through the gastric juice and allows the controlled release of the active ingredient in an alkaline or neutral aqueous medium, corresponding to the conditions found in the part near to the small intestine.

The invention also provides a method for the prevention and treatment of disorders related to the abnormal secretion of gastric acid that comprises the administration to the affected patient of a therapeutically effective amount of the pharmaceutical formulation of the invention.

The following examples serve to illustrate the invention. The tests of release of the active ingredient were carried out following the protocol described in Monograph 724 of the USP for "Drug Release", in particular for Delayed-release (Enteric coated Articles)

EXAMPLE 1

A suspension of the active ingredient is prepared by dispersing 80.40 g of active ingredient [omeprazole or lansoprazole], 64.33 g of HPMC and 20.12 g of talc, in 642.86 g of purified water (deionized).

563.03 g of inert, spherical, uniform saccharose nuclei of between 1.0 and 1.2 mm are introduced into a fluid bed apparatus, over which the previously prepared suspension is sprayed. After spraying, and before applying the second layer, the spheres obtained (the inert nuclei covered with the active layer) are dried.

60.54 g of HPMC, 8.04 g of talc and 8.03 g of titanium dioxide are dispersed in 402.86 g of purified water, and the resulting aqueous suspension sprayed over the previously prepared spheres. After spraying, and before applying the following layer, the spheres thus obtained are dried.

36.20 g of HPMC and 44.25 g of an aqueous dispersion of ethylcellulose (EC) (ratio of EC:HPMC 55:45) are dispersed in 631.43 g of purified water and the resulting aqueous suspension sprayed over the previously obtained spheres. After spraying, and before applying the following layer, the spheres thus obtained are dried.

88.50 g of copolymer of methacrylic acid of USP/Ph.Eur quality (aqueous dispersion type C), 13.28 g of triethyl citrate and 13.28 g of talc are dispersed in 285.71 g of purified water, and the resulting aqueous suspension sprayed over the previously obtained spheres. After applying this layer of enteric coating the resulting spheres (pellets) are dried. The pellets obtained have a slow release profile.

EXAMPLE 2

The procedure described in Example 1 was repeated with the exception that the suspension that contained the components of the intermediate layer of modified release contained 24.14 g of HPMC and 56.31 g of an aqueous dispersion of EC (ratio of EC:HPMC 70:30). The pellets obtained have a very slow release profile.

EXAMPLE 3

A suspension of active ingredient was prepared dispersing 81.79 g of active ingredient [omeprazole or lansoprazole], 62.91 g of HPMC and 19.66 g of talc, in 629.10 g of purified water (deionized).

547.34 g of inert, spherical, uniform saccharose nuclei of between 1.0 and 1.2 mm are introduced into a fluid bed apparatus, over which the previously prepared suspension is sprayed. After spraying, and before applying the second layer, the spheres obtained (the inert nuclei covered with the active layer) are dried.

58.98 g of HPMC, 7.86 g of talc and 7.86 g of titanium dioxide are dispersed in 393.20 g of purified water, and the resulting aqueous suspension sprayed over the previously prepared spheres. After spraying, and before applying the following layer, the spheres thus obtained are dried.

39.32 g of HPMC and 39.32 g of an aqueous dispersion of ethylcellulose (EC) (ratio of EC:HPMC 50:50) are dispersed in 786.40 g of purified water and the resulting aqueous suspension sprayed over the previously obtained spheres. After spraying, and before applying the following layer, the spheres thus obtained are dried.

103.81 g of copolymer of methacrylic acid of USP/Ph.Eur quality (aqueous dispersion type C) [Eudragit® L30D], 15.57 g of triethyl citrate [Eudraflex®] and 15.59 g of talc are dispersed in 332.20 g of purified water, and the resulting aqueous suspension sprayed over the previously obtained spheres. After applying this layer of enteric coating the resulting spheres (pellets) are dried. The pellets obtained have a slow release profile.

EXAMPLE 4

The procedure described in Example 3 was repeated with the exception that the suspension that contained the components of the intermediate layer of modified release contained 31.46 g of HPMC and 47.18 g of an aqueous dispersion of EC (ratio of EC:HPMC 60:40). The pellets obtained have a slow release profile.

EXAMPLE 5

The procedure described in Example 3 was repeated with the exception that the suspension that contained the components of the intermediate layer of modified release contained 23.59 g of HPMC and 55.05 g of an aqueous dispersion of EC (ratio of EC:HPMC 70:30). The pellets obtained have a very slow release profile.

EXAMPLE 6

A suspension of the active ingredient is prepared by dispersing 402 g of active ingredient [omeprazole or lansoprazole], 321.65 g of HPMC and 100.6 g of talc, in 3,214.3 g of purified water (deionized).

2,815.15 g of inert, spherical, uniform saccharose nuclei of between 1.0 and 1.2 mm are introduced into a fluid bed apparatus, over which the previously prepared suspension is sprayed. After spraying, and before applying the second layer, the spheres obtained (the inert nuclei covered with the active layer) are dried.

302.7 g of HPMC, 40.2 g of talc and 40.15 g of titanium dioxide are dispersed in 2,014.3 g of purified water, and the resulting aqueous suspension sprayed over the previously prepared spheres. After spraying, and before applying the following layer, the spheres thus obtained are dried.

162.91 g of HPMC and 957.36 g of an aqueous dispersion of ethylcellulose (EC) (ratio of EC:HPMC 85:15) are dispersed in 3,157.15 g of purified water and the resulting aqueous suspension sprayed over the previously obtained spheres. After spraying, and before applying the following layer, the spheres thus obtained are dried.

1,475 g of copolymer of methacrylic acid of USP/Ph.Eur quality (aqueous dispersion type C) [Eudragit® L30D], 66.4 g of triethyl citrate [Eudraflex®] and 66.4 g of talc are dispersed in 1,428.55 g of purified water, and the resulting aqueous suspension sprayed over the previously obtained spheres. After applying this layer of enteric coating the resulting spheres (pellets) are dried. The pellets obtained have the nucleus and 4 layers (active, inert coating, modified release and enteric) and a very slow release profile.

EXAMPLE 7

A suspension of the active ingredient is prepared by dispersing 402 g of active ingredient [omeprazole or lansoprazole], 321.65 g of HPMC and 100.6 g of talc, in 3,214.3 g of purified water (deionized).

2,815.15 g of inert, spherical, uniform saccharose nuclei of between 1.0 and 1.2 mm were introduced into a fluid bed apparatus, over which the previously prepared suspension was sprayed. After spraying, and before applying the second layer, the spheres obtained (the inert nuclei covered with the active layer) are dried.

465.61 g of HPMC, 40.2 g of talc, 40.15 g of titanium dioxide and 957.36 g of an aqueous dispersion of EC [ratio of EC:HPMC 67:33] are dispersed in 5,171.45 g of purified water, and the resulting aqueous suspension sprayed over the previously prepared spheres. After spraying, and before applying the following layer, the spheres thus obtained are dried.

1,475 g of copolymer of methacrylic acid of USP/Ph.Eur quality (aqueous dispersion type C) [Eudragit® L30D], 66.4 g of triethyl citrate [Eudraflex®] and 66.4 g of talc are dispersed in 1,428.55 g of purified water, and the resulting aqueous suspension sprayed over the previously obtained spheres. After applying this layer of enteric coating the resulting spheres (pellets) are dried. The pellets obtained have the nucleus and 3 layers [active, intermediate (formed by the inert coating and the modified release system) and enteric] and a very slow release profile.

EXAMPLE 8

RELEASE OF THE ACTIVE INGREDIENT

Following the methodology described in the preceding Examples different batches of pellets of omeprazole have been prepared with different systems of modified release changing only the relative quantities of EC and HPMC with the aim of modifying the ratio of EC:HPMC.

The protocol used in the release assay of the active ingredient is described in Monograph 724 of the USP for "Drug Release", in particular for Delayed-Release (Enteric coated Articles). The percentage of omeprazole released at different times in aqueous medium (pH 6.8) was determined after having previously kept the different pellets for 2 hours in HCl medium.

The results obtained are shown in Table 1.

TABLE 1

Percentage of release of Omeprazole from pellets with differing release profiles

| Time (minutes) | Pellets with quick release profile [EC:HPMC] = 55:45 | Pellets with slow release profile [EC:HPMC] = 70:30 |
| --- | --- | --- |
| 0 | 0 | 0 |
| 120 | 0.4 | 0.8 |
| 125 | 2.6 | 2 |
| 130 | 34.6 | 2.8 |
| 135 | 70.8 | 5.3 |
| 140 | 90.5 | 11.1 |
| 150 | 92.2 | 25.9 |
| 165 | 98.3 | 47.2 |
| 185 | 100 | 58.2 |
| 210 | 100 | 73 |
| 240 | 100 | 80.8 |

This assay demonstrated how increasing the amount of EC with respect to the amount of HPMC present in the modified release system led to pellets with slower release profiles of the active ingredient.

What is claimed is:

1. A pellet comprising an acid labile benzimidazole compound, wherein the pellet comprises:

(a) an inert nucleus;

(b) a layer disposed over said inert nucleus (a), consisting of an acid labile benzimidazole compound, an inert, non-alkaline polymer soluble in water and one or more pharmaceutically acceptable inert excipient, wherein said inert excipients do not react in the conditions used;

(c) one or more intermediate layers that comprise:

(i) an inert, non-alkaline coating, formed of an inert, non-alkaline polymer soluble in water and one or more pharmaceutically acceptable inert excipients; and (ii) a system of modified release that comprises an inert, non-alkaline polymer soluble in water and an inert polymer insoluble in water, wherein the weight ratio of the inert, non-alkaline polymer soluble in water to the inert polymer insoluble in water is 50:85 to 15:50; said intermediate layer(s) (c) disposed over said layer (b) that covers the inert nucleus; and (d) an external layer comprising an enteric coating disposed over said intermediate layer(s) (c).

2. A pellet according to claim 1 wherein said one or more intermediate layers (c) comprise one or more layers of an inert, non-alkaline coating and one or more layers of a system of modified release.

3. A pellet according to claim 1 wherein the inert, non-alkaline coating and the system of modified release are mixed in a single layer.

4. A pellet according to claim 1, in which said one or more intermediate layers (c) comprise a mixture of one or more layers of inert, non-alkaline coating, and one or more layers of said system of modified release that comprises an inert, non-alkaline polymer soluble in water and an inert polymer insoluble in water, and one or more layers of a mixture of inert, non-alkaline coating, and said system of modified release that comprises an inert, non-alkaline polymer soluble in water and an inert polymer insoluble in water.

5. A pellet according to claim 1, wherein the inert, non-alkaline coating, formed of an inert, non-alkaline polymer soluble in water and one or more pharmaceutically acceptable inert excipients is disposed over the layer (b), wherein the layer comprises the system modified release that comprises an inert, non-alkaline polymer soluble in water and an inert polymer insoluble in water which is disposed over the layer of the inert, non-alkaline coating; and the layer (d) is disposed over the layer formed by the system of modified release comprising an inert non-alkaline polymer soluble in water and an inert polymer insoluble in water.

6. A pellet according to claim 1 wherein said acid labile benzimidazole compound is a compound of formula (I)

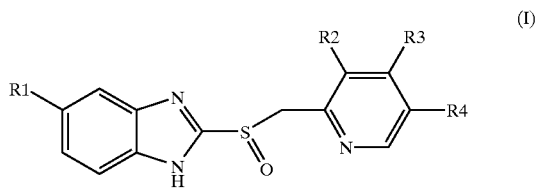

wherein
R$^1$ is hydrogen methoxy or difluoromethoxy;
R$^2$ is methyl or methoxy;
R$^3$ is methoxy, 2,2,2-trifluoroethoxy or 3-methoxypropoxy; and
R$^4$ is hydrogen or methyl.

7. A pellet according to claim 1 wherein said acid labile benzimidazole compound is selected from the group consisting of omeprazole, lansoprazole, pantoprazole and mixtures thereof.

8. A pellet according to claim 1 wherein said inert, non-alkaline polymer soluble in water, present in the layer (b) is selected from hydroxypropylmethylcellulose (HPMC) and hydroxypropylcellulose (HPC).

9. A pellet according to claim 1, wherein said inert, non-alkaline polymer soluble in water of the inert, non-alkaline coating, present in the intermediate layer(s) (c) is hydroxypropylmethylcellulose (HPMC).

10. A pellet according to claim 1 wherein said inert, non-alkaline polymer soluble in water of the system of modified release, present in the one or more intermediate layers (c) is hydroxypropylmethylcellulose (HPMC).

11. A pellet according to claim 1 wherein said inert polymer insoluble in water of the system of modified release, present in the one or more intermediate layers (c) is ethylcellulose or a copolymer of ammonium methacrylate.

12. A pellet according to claim 1 wherein said external layer (d) comprises a gastro-resistant polymer, a plasticizer and one or more pharmaceutically acceptable inert excipients.

13. A composition of modified release that comprises one or more pellets of claim 1.

14. A composition of modified release comprising a mixture of the pellets of claim 1 having the same release profile.

15. A composition of modified release comprising a mixture of the pellets of claim 1 having a different release profile.

16. A composition of modified release comprising a mixture of the pellets of claim 1 which have (i) a quick release profile and (ii) a slow release profile in a ratio between 10:90 and 90:10 by weight.

17. A composition according to claim 13, in the form of a capsule or a tablet.

18. A method for obtaining a gastro-resistant pellet of modified release that contains as an active ingredient an acid labile benzimidazole compound, that comprises:

(i) applying an aqueous suspension of an acid labile benzimidazole compound, an inert, non-alkaline polymer soluble in water, and one or more pharmaceutically acceptable inert excipients to cover an inert nucleus, wherein said inert excipients do not react in the conditions used;

(ii) applying one or more intermediate layers, separated or mixed among themselves that contain (i) an inert, non-alkaline coating, formed of an inert, non-alkaline polymer soluble in water and one or more pharmaceutically acceptable inert excipients; and (ii) a system of modified release that comprises an inert, non-alkaline polymer soluble in water and an inert polymer insoluble in water, wherein the weight ratio of the inert, non-alkaline polymer soluble in water to the inert polymer insoluble in water is 50:85 to 15:50 a plasticizer and an anti-tack agent, separate or mixed; and (iii) covering said intermediate layer or layers with an aqueous suspension that comprises a gastro-resistant polymer, a plasticizer and one or more pharmaceutically acceptable inert excipients to create an external layer of enteric coating.

19. A method according to claim 18 wherein said acid labile benzimidazole compound is a compound of formula (I)

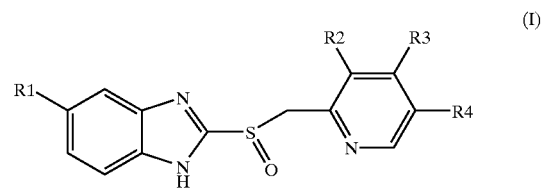

wherein
R$^1$ is hydrogen, methoxy or difluoromethoxy;
R$^2$ is methyl or methoxy;
R$^3$ is methoxy, 2,2,2-trifluoroethoxy or 3-methoxypropoxy; and
R$^4$ is hydrogen or methyl.

20. A method according to claim 18 wherein said acid labile benzimidazole compound is selected from the group consisting of omeprazole, lansoprazole, pantoprazole and mixtures thereof.

21. A method according to claim 18, wherein, said inert, non-alkaline polymer soluble in water, present in the suspension applied in step (i) is selected from hydroxypropylmethylcellulose (HPMC) and hydroxypropylcellulose (HPC).

22. A method according to claim 18, wherein, said inert, non-alkaline polymer soluble in water, comprised in the inert, non-alkaline coating, present in the suspension applied in step (ii) is hydroxypropylmethylcellulose (HPMC).

23. A method according to claim 18, wherein, said inert, non-alkaline polymer soluble in water, comprised in the system of modified release, present in the suspension applied in step (ii) is hydroxypropylmethylcellulose (HPMC).

24. A method according to claim 18 wherein said inert polymer insoluble in water, comprised in the system of modified release, present in the suspension applied in step (ii) is ethylcellulose or a copolymer of ammonium methacrylate.

* * * * *

UNITED STATES PATENT AND TRADEMARK OFFICE
CERTIFICATE OF CORRECTION

PATENT NO. : 6,780,436 B1
DATED : August 24, 2004
INVENTOR(S) : Antonio López-Cabrera et al.

It is certified that error appears in the above-identified patent and that said Letters Patent is hereby corrected as shown below:

Column 10,
Line 59, delete "excipient" insert -- excipients --

Column 11,
Line 3, delete "50:85" insert -- 0.18 to 1:1 (15/85 to 50/50) --
Line 4, delete "5:50"
Lines 19-22, delete ", and one or more layers of a mixture of inert, non-alkaline coating, and said system of modified release that comprises an inert, non-alkaline polymer-soluble in water and an inert polymer insoluble in water"
Line 27, insert -- of -- between "modified" and "release"
Line 46, insert -- , -- between "hydrogen" and "methoxy"

Column 12,
Line 40, delete "50:85 to 15:50" insert -- 0.18 to 1:1 (15/85 to 50/50), --

Signed and Sealed this

Twenty-second Day of March, 2005

JON W. DUDAS
*Director of the United States Patent and Trademark Office*